United States Patent [19]

Sjoerdsma

[11] Patent Number: 4,670,459
[45] Date of Patent: Jun. 2, 1987

[54] METHOD OF ALLEVIATING WITHDRAWAL SYMPTOMS

[75] Inventor: Albert Sjoerdsma, Cincinnati, Ohio

[73] Assignee: Merrell Dow Pharmaceuticals Inc., Cincinnati, Ohio

[21] Appl. No.: 821,668

[22] Filed: Jan. 23, 1986

Related U.S. Application Data

[60] Division of Ser. No. 657,288, Oct. 3, 1984, Pat. No. 4,575,570, which is a division of Ser. No. 467,553, Feb. 17, 1983, abandoned, which is a continuation-in-part of Ser. No. 330,529, Dec. 14, 1981, Pat. No. 4,382,946.

[51] Int. Cl.$^4$ ............................................. A61K 31/415
[52] U.S. Cl. ..................................... 514/401; 514/812
[58] Field of Search ................................ 514/401, 812

Primary Examiner—Stanley J. Friedman
Attorney, Agent, or Firm—Raymond A. McDonald

[57] ABSTRACT

The use of lofexidine and its pharmaceutically acceptable salts in alleviating the adverse symptoms of drug withdrawal, pre-menstrual tension and peri-menopausal flushing is disclosed.

8 Claims, No Drawings

METHOD OF ALLEVIATING WITHDRAWAL SYMPTOMS

This application is a division of Ser. No. 657,288, filed Oct. 3, 1984, now U.S. Pat. No. 4,575,570, which is a division of Ser. No. 467,553, filed Feb. 17, 1983, now abandoned, which is a continuation-in-part of Ser. No. 330,529, filed Dec. 14, 1981, now U.S. Pat. No. 4,382,946.

BACKGROUND OF THE INVENTION

One of the major problems facing our society today is the widespread use of addicting drugs by a great many individuals. Among the drug abuse problems in the United States, alcoholism is the most serious in terms of economic loss, loss in productivity and psychological damage to individuals and families. An estimated ten million people in this country are afflicted with serious drinking problems.

Second in importance is the dependence of an ever increasing segment of our population upon narcotic drugs, particularly among the younger people. In 1970 J. Ingersoll suggested that there are from 120,000 to 180,000 heroin users in this country alone, i.e., a ratio of 1 in 1,100 to 1 in 1,700 persons (Statement before the U.N. Commission on Narcotic Drugs, Sept. 28, 1970).

Again, the habit forming tendencies of tobacco are well known, as are the symptoms of tobacco withdrawal. Moreover, it is now well documented that tobacco consumption, particularly in the form of cigarette smoking, is hazardous to one's health. Smoking has been implicated as a causative agent in such conditions as emphysema, lung, mouth and throat cancer, the aggravation of hypertension, atherosclerosis and in coronary artery disease. Of the millions of people in this country who voluntarily attempt to give up smoking each year, the long term success rate at present is only 3%.

There appears to be no common denominator for the dependency of these various drug substances. Drug dependency occurs in people of all ages, having diverse backgrounds and at every socio-economic level. The one generalization that can be made, however, is that following a period of drug dependency, most individuals seek to escape their drug dependency but find it extremely difficult to do. This is true whether the dependency is one based on narcotic substances, other drugs, tobacco or alcohol. In the case of narcotics substances, and in particular opiates, withdrawal is virtually impossible absent controlled and carefully monitored hospital treatment. Moreover, the severe withdrawal symptoms that are endured, frequently have a deleterious effect upon the physical, mental and emotional well-being of the individual. In the case of alcoholism, multiple detoxifications during the course of an individual's lifetime are the rule.

Inasmuch as opiates and other drugs have certain behavioral and biochemical effects which appear to involve catecholamine neurotransmitter systems, investigators have tried to mimic the withdrawal of these drugs by administering drugs which antagonize these transmitter systems. U.S. Pat. No. 3,923,987 illustrates one such attempt using pharmaceutical compositions consisting of N-(furyl or thienylmethyl)-14-oxy-7,8-dihydronormorphinone or norcodeinone in an effort to antagonize the effects of opiate dependency. Deoxycytidine, a morphine antagonist, is also stated to be useful for the treatment of morphine addiction and toxification, see U.S. Pat. No. 3,873,698.

These approaches have not met with much success, however, and the usual treatment for narcotic or opiate withdrawal involves maintenance therapy. Maintenance therapy is a relatively new approach to narcotic addiction, pioneered predominately by Dole and Co-workers (Arch. Int. Med. 118, 304 (1966); J. Am. Med. Assn., 206, 2708 (1968) and New. Engl. J. Med. 280, 1372 (1969), wherein a narcotic substitute is administered in lieu of the drug substance. The narcotic substitute most frequently used in maintenance therapy is methadone, more particularly the hydrochloride salt of methadone.

Detoxification via methadone maintenance, however, is a slow and difficult process with patients frequently experiencing abstinence and withdrawal symptoms due to methadone itself. Moreover, methadone maintenance is potentially subject to abuse when administered intravenously so as to obtain potentiated narcotic effects.

Recent studies have shown that clonidine, 2-(2,6-dichloroanilino)-2-imidazoline relieves certain symptoms of opiate withdrawal, Washton et al., Lancet, pp. 1078-9 (1980) and Gold et al., J. Am. Med. Assn. 243, pp. 343-6 (1980). Additionally, clonidine has been suggested as a useful aid in the treatment of alcohol withdrawal, Bjorkqvist, Acta Psychiat. Scand. 52, pp. 256-63 (1975). However, due to oversedation and the potentially serious decrease in blood pressure in some patients, this method of detoxification requires the close supervision of an inpatient setting. Moreover, many patients develop a tolerance to the sedative effect of clonidine after several days and require additional night time sedation to alleviate insomnia.

Thus, it can be seen that there exists an urgent need for a drug that is useful in alleviating the effects of withdrawal from a wide variety of addicting drug substances, which drug is safe and non-addicting in and of itself, and which does not possess the serious disadvantages of some of the compounds used in the past for this purpose.

SUMMARY OF THE INVENTION

The present invention relates to a method of treating drug dependent individuals who wish to eliminate their drug dependency. More particularly, this invention relates to the alleviation of the effects of drug withdrawal by the administration of lofexidine to individuals who are dependent upon such drugs or drug substances as alcohol, tobacco, opium, heroin, barbiturates, benzodiazepines and methadone. In addition, this invention relates to the alleviation of drug-like withdrawal symptoms wherein the adverse symptoms are those associated with pre-menstrual tension and peri-meanopausal flushing. A preferred embodiment of this invention is the use of lofexidine in alleviating the adverse symptoms of alcohol withdrawal in the treatment of alcoholism.

In accordance with the present invention it has been discovered that when an individual or patient undergoes withdrawal from harmful addictive drugs, the withdrawal syndrome created by the complete abstinence of the addicting drug can be alleviated or materially minimized by the administration of an anti-withdrawal effective amount, or drug antagonistic effective amount, of lofexidine. By using lefexidine in accordance with the teachings of this invention, some or all of the withdrawal symptoms that might normally be encountered are alleviated or eliminated.

Thus, the present invention provides a method of alleviating or minimizing the adverse symptoms of withdrawal from the aforementioned drugs, thereby making it easier for a drug dependent individual to rid himself of his drug dependency.

In addition, the rapid lowering of circulating hormone levels in women experiencing pre-menstrual syndrome, and in man or women experiencing menopause, frequently results in adverse symptoms that are similar to those which an individual or patient experiences while undergoing withdrawal from addictive drugs. Accordingly, this invention also provides a method of alleviating or easing the adverse symptoms associated with pre-menstrual tension and peri-menopausal flushing.

DETAILED DESCRIPTION OF THE INVENTION

Whereas clonidine has been found to be useful in easing the pain and discomfort of opiate withdrawal in patients attempting to detoxify from heroin or methadone addiction, the potent sedative and antihypertensive effects of this drug limits its usefulness.

Lofexidine, 2-[α-(2,6-dichlorophenoxy)ethyl]-$\Delta^2$-imidazoline, is an experimental compound which is related to clonidine. Like clonidine, lofexidine has been found to have antihypertensive activity in man, Burke et al. Clin. Pharmacol. Therap. 21, pp. 99-100 (1977). Additionally, lofexidine has recently been reported to block morphine withdrawal signs in addicted rats, Pharmacol. Biochem. Behav. 12, pp. 573-5 (1979).

I have now found that lofexidine is extremely effective in alleviating or minimizing many of the symptoms associated with drug withdrawal. In particular, lofexidine is useful in alleviating the adverse symptoms most frequently associated with alcohol and narcotic withdrawal.

The term drug or drug substance as used herein is intended to encompass those addicting drugs or drug substances including alcohol, tobacco, opium, heroin, methadone, barbiturates such as phenobarbital, secobarbital or pentobarbital, and benzodiazepines such as chlordiazepoxide or diazepam. In addition, for purposes of this invention, the term drug or drug substance is intended to include those hormones or biochemical agents which are physiologically responsible for the drug-like withdrawal symptoms associated with pre-menstrual tension and peri-menopausal flushing.

The various withdrawal symptoms that are alleviated in accordance with the teachings of this invention will, of course, vary depending upon the particular type of addiction being treated. Moreover, these symptoms will also vary depending upon such factors as age, sex and extent and degree of the individual's drug dependency.

In many cases of alcoholism and narcotic withdrawal, the patient first becomes functional a week or more following cessation of the addicting drug. Accordingly, before any rehabilitation or proper medical treatment can occur, the physician must frequently wait a week or more post-drug withdrawal until the patient has become stabilized. One of the principal advantages of the present invention is the rapid onset of improvement in patients undergoing withdrawal symptoms. Thus, in some instances, patients are practically asymptomatic after 48 hours of lofexidine therapy, thereby enabling rehabilitation to occur earlier resulting in a shorter in-patient period.

Some of the adverse symptoms associated with drug withdrawal which are alleviated in the practice of this invention are: eating disturbances, vomiting, nausea, diarrhea, sweating, flushing, hypertension, insomnia, convulsions, tremors, lethargy, muscle/bone pains, cramps, tinnitus, anxiety, depression, tension, hallucinations, nightmares, delusions, fever, garbled speech, weakness, apprehension, heightened emotional tone, confusion, tachycardia and, of course, an intense craving for the addicting drug. For persons undergoing pre-menstrual tension or peri-menopausal flushing related symptomology such as: dizziness, lightheadedness, irritability, nervousness, dry mouth, increased thirst or appetite, depression, headache, swelling, stiffness, oldema or sleepiness, is also alleviated in the practice of this invention.

The alleviation of these adverse symptoms of drug withdrawal can be conveniently established using outpatient drug-dependent volunteers. Inasmuch as many of these adverse symptoms above are subjective in nature, the efficacy of lofexidine is determined on the basis of a comparison of various withdrawal symptom scales. In general, various symptoms are noted and numerical values ranging from 0 (none) to 10 (severe) are assigned thereto by the patient and totaled. Total scores are compared before, during and after withdrawal. Where possible these scores are accompanied by physical and laboratory examinations including blood pressure and electrocardiogram determinations under the supervision of a physician.

In the case of narcotic withdrawal, subjects who report no illicit narcotic use during the preceding 10 days receive a naloxone challenge on day 11. Naloxone is a narcotic antagonist which will precipitate a withdrawal reaction when given to individuals dependent upon narcotics. In subjects who reported that they have used an illicit narcotic, the naloxone challenge is postponed until it poses a minimal risk of precipitating a withdrawal reaction in the patient. Subjects who pass the naloxone challenge are treated with naltrexone, a milder narcotic antagonist, and are then considered to be successfully detoxified.

In the case of tobacco withdrawal, outpatient data is considered to be unreliable. Thus, data is gathered from patients who are generally hospitalized for medical reasons relating primarily to pulmonary disease, and from patients who have a history of smoking at least 20 cigarettes per day for one year or more. Lofexidine or placebo (in the case of double-blind studies) are administered and physical signs, such as blood and urine, are monitored. Additionally, self-evaluation scales relating to specific withdrawal symptoms including appetite, mood, attention span, sleep characteristics and craving for tobacco are recorded daily. Abstinence from tobacco for a period of 3 months is generally considered a cure.

Lofexidine can be incorporated in any suitable manner with a pharmaceutically acceptable carrier for administration to the patient. The compound can be orally administered in the form of a suspension, elixir, powder, capsule, tablet, lozenge and the like, or it may be administered parenterally. The preferred mode of administration is oral via a capsule, tablet or powder mix that can be dissolved in a liquid.

The pharmaceutical vehicle or carrier to be employed can include any inert or excipient material normally employed in pharmaceutical compositions, such as, for example, binders, fillers, lubricants, stabilizers, preservatives, retardants, buffers, colors, etc. Examples of such materials are cellulose derivatives such as, for example, microcrystalline cellulose, carboxymethyl cellulose, etc.; starches such as, for example, potato, maize, wheat, arrowroot, amylopectine etc.; sugars such as, for example, lactose, sucrose, sacchrose and; other ingredients such as, for example, gelatine, calcium phosphate, stearic acid, talc, mannitol, sorbitol, calcium stearate, magnesium stearate, polyethylene glycols, agar, gum acacia, etc. Film coatings, enteric coatings and compositions wherein the active ingredient lofexidine has been formulated as a sustained release preparation can also be favorably employed in the practice of this invention.

The dosage of an anti-withdrawal effective amount of lofexidine is that amount of lofexidine which when administered to a drug dependent individual will alleviate the adverse symptoms of withdrawal without adversely effecting the blood pressure of such an individual. Such an anti-withdrawal effective amount varies from individual to individual depending upon the age, sex, weight, type, degree and length of drug dependency. Stating this another way, an anti-withdrawal effective amount is that amount of lofexidine which will antagonize the effects of drug withdrawal in a drug dependent individual.

Generally, this amount of lofexidine ranges from about 0.1 mg to about 2.4 mg per day. In the treatment of methadone and narcotic withdrawal, the amount of lofexidine employed preferably rages from about 0.4 mg to about 2.4 mg per day. In the treatment of alcohol withdrawal, the amount of lofexidine employed preferably ranges from about 0.4 mg to about 2.4 mg per day. For use in the treatment of tobacco withdrawal, the amount of lofexidine employed preferably ranges from about 0.1 mg to 1.0 mg per day.

Lofexidine can be conveniently administered in tablet or capsule dosage unit forms. Preferably, lofexidine is administered daily in multiple dosage unit forms containing 0.1 mg of lofexidine each. Even more preferred in the practice of this invention is the administration of the requisite number of film coated tablets, containing 0.1 mg of lofexidine each, administered three to four times daily.

Without futher elaboration, it is believed that one skilled in the art can practice the present invention to its fullest extent utilizing the preceding description. The following examples are, therefore, merely illustrative of the invention, and are not to be construed as limiting the invention in any manner whatsoever.

EXAMPLE 1

Tablet Preparation

One thousand film coated tablets for oral use, each tablet containing 0.1 mg or 0.2 mg of lofexidine, are prepared in accordance with the following formulation:

| Core Tablet Ingredients | 0.1 mg Tablet (gms) | 0.2 mg Tablet (gms) |
| --- | --- | --- |
| Lofexidine hydrochloride | 0.1 | 0.2 |
| Lactose | 138 | 137.9 |
| Citric acid | 18.5 | 18.5 |
| Povidone | 1.6 | 1.6 |
| Microcrystalline cellulose | 8.5 | 8.5 |
| Calcium stearate | 2.1 | 2.1 |
| Sodium lauryl sulfate | 1.1 | 1.1 |
| Purified Water | q.s. | q.s. |

| Film Coating Ingredients | Grams |
| --- | --- |
| Opaspray ® K-1-2228, mixture of dyes, TiO$_2$ and hydroxypropyl cellulose | 1.8 |
| Hydroxypropyl methylcellulose | 1.8 |
| Methylene chloride | 60.0 |
| 3A Alcohol | 13.5 |

Citric acid is milled and the milled powder added to the lactose in a suitable mixer. Lofexidine and povidone are dissolved in approximately 10 ml of water and used to granulate the citric acid-lactose mixture. The granulation so prepared is wet screened and the granules dried and ground. Calcium stearate, sodium lauryl sulfate and microcrystalline cellulose are added, mixed and the resulting mixture compressed into tablets.

The coating suspension is prepared by dissolving hydroxypropyl methylcellulose in methylene chloride. The alcohol and Opaspray are added and the suspension homogenized. Core tablets are warmed in a baffled rotating coating pan and the coating applied via intermittent spraying and drying until a suitable tablet coat is obtained.

EXAMPLE 2

Capsule Preparation

One thousand two piece hard gelatin capsules for oral use are prepared as follows:

| Ingredients | Grams |
| --- | --- |
| Lofexidine hydrochloride | 0.1 |
| Lactose | 197.9 |
| Magnesium stearate | 2.0 |

The above formulation is prepared by passing each of the dry powders through a fine mesh screen. The lofexidine hydrochloride is thoroughly distributed in the lactose and the magnesium stearate added. All of the powders are well mixed and filled via conventional techniques into No. 4 two-piece hard gelatin capsules having a net fill of 200 mg each. Each capsule so prepared contains 0.1 mg of lofexidine hydrochloride.

EXAMPLE 3

Powder Mix For Oral Solution

| Ingredients | Grams |
| --- | --- |
| Lofexidine hydrochloride | .01 |
| Lactose | 199.9 |

The above formulation is prepared by passing each of the dried powders through a fine screen and the lofexidine hydrochloride is thoroughly distributed in the lactose. One teaspoon of the above powder when dissolved in water or juice is equivalent to a dosage of approximately 0.2 mg of lofexidine hydrochloride.

EXAMPLE 4

Alcohol Withdrawal

Eleven alcohol dependent patients who have expressed a desire to be detoxified and who are not currently using tricyclic antidepressant, MAO inhibitor or neuroleptic drugs are given an initial morning dose of 0.2 mg of lofexidine. This is followed in about two hours by a 0.1 mg dose of lofexidine, if necessary. The next dose is administered approximately 8 hours after the first dose and ranges from 0.2–0.4 mg of lofexidine depending upon the patient's response to earlier doses. The final dose of the day is administered approximately 16 hours after the first dose and ranges from 0.2–0.5 mg of lofexidine depending upon the patient's response to earlier doses.

The second and final day of dosing comprises three doses of from 0.2 to 0.5 mg of lofexidine, depending upon the optimum dose on day 1, administered approximately 8 hours apart.

The following observations are taken and evaluated immediately prior to the first dosage, six and twelve hours after the first dosage, and then once each day for the duration of the study: Brief Psychiatric Rating Scale (BPRS), Overall and Gorham, Psychol. Rep., 10:799–812, 1962, the Fabre-McLendon Alcohol Withdrawal Symptom Scale (FMS), the McLendon-Fabre Self-Rating Alcohol Withdrawal scale (MFS), and the Alcohol Withdrawal Symptom Scale (AWSS). The various symptoms observed are numerically rated on the basis of pre-determined values, in which the symptoms are rated according to their presence or absence, and if present in accordance with their intensity. The mean scores for all eleven patients treated with lofexidine are as follows:

| Rating Score | Pre-Drug Score Mean + S.D. | 48 Hour Score Mean + S.D. |
| --- | --- | --- |
| MFS | 30.6 ± 8.7 | 13.2 + 7.8* |
| FMS | 13.2 ± 1.1 | 5 ± 2.4* |
| AWSS | 24.7 ± 5.7 | 11.1 ± 6.2* |
| BPRS | 13.7 ± 1.2 | 9.4 ± 2.0* |

*Value is significantly (P 0.05) different from the corresponding pre-drug value.

Comparison of the mean pre-drug scores with those scores obtained following 48 hours of treatment with lofexidine demonstrate a marked decrease in withdrawal symptoms for all four rating scales which is statistically significant. Moreover, the patients are relatively asymptomatic after only 48 hours of lofexidine therapy, whereas other modalities of treatment generally require 7 days to achieve this degree of symptomatic relief.

EXAMPLE 5

Methadone Withdrawal

Fifteen methadone-dependent (10–25 mg/day) outpatients who who have exhibit no serious medical or psychiatric illness and who have expressed a desire to undergo detoxification are given the following regimen.

On day 1 the patients receive their usual methadone dose and begin a self-administered regimen of 0.1 to 0.4 mg of lofexidine. On day 2, methadone is abruptly discontinued by the substitution of placebo. During the course of this study, the dosage of lofexidine is increased as necessary for individual patients, in accordance with the symptoms observed, up to a maximum of 1.6 mg/day. Blood pressure, withdrawal symptoms, and lofexidine effects are assessed daily. Subjective ratings of lofexidine effectiveness in alleviating various pharmacological effects are recorded on a scale ranging from zero (no withdrawal suppression) to ten (complete suppresion).

Those subjects who report no illicit opiate usage during the preceding 10 days are given a naloxone challenge on day 11 (2.0 mg I.V.) to confirm opiate free status. Naloxone when given to narcotic dependent individuals precipitates a withdrawal reaction. Subjects who report that they have used illicit opiates during the first 10 days post-methadone treatment are permitted to continue on lofexidine. Additionally, the naloxone challenge is postponed in those patients to a time at which it poses a minimal risk of precipitating a withdrawal reaction. Subjects who pass the naloxone challenge are started on naltrexone, a mild narcotic antagonist. Patients who receive naltrexone at days 11–21 are considered successful detoxifications, whereas patients who return to opiate or methadone use and fail to begin naltrexone are considered unsuccessful detoxifications. The results are summarized as follows.

| Patient No. | Methadone Level (mg) | Days On Lofexidine | Highest Lofexidine Dose (mg) | Mean Effectiveness Rating[a] | Patient's Subjective Evaluation[b] | Physician's Evaluation[c] | Treatment Outcome[d] |
| --- | --- | --- | --- | --- | --- | --- | --- |
| 1 | 20 | 21 | 1.6 | 5.25 | Much | Moderate | Success |
| 2 | 20 | 12 | 0.9 | 4.9 | No info. | Moderate | Success |
| 3 | 20 | 10 | 0.6 | 6.6 | Very much | Moderate | Success |
| 4 | 20 | 4 | 0.6 | 7.0 | Much | Moderate | Dropout |
| 5 | 10 | 7 | 0.6 | 8.8 | Very much | Marked | Dropout |
| 6 | 10 | 3 | 0.8 | 7.0 | A little | Minimal | Dropout |
| 7 | 20 | 10 | 1.2 | 8.9 | Very much | Marked | Success |
| 8 | 10 | 10 | 1.6 | 8.1 | Very much | Marked | Success |
| 9 | 10 | 11 | 1.6 | 8.9 | Very much | Marked | Success |
| 10 | 20 | 19 | 1.4 | 8.7 | Very much | Marked | Success |
| 11 | 20 | 4 | 1.4 | 3.1 | Moderately | Moderate | Dropout |
| 12 | 10 | 12 | 1.5 | 8.9 | Very much | Marked | Success |
| 13 | 25 | 19 | 1.5 | 8.8 | Moderately | Minimal | Failure |
| 14 | 20 | 15 | 1.5 | 8.0 | No info. | No Info. | Dropout |
| 15 | 20 | 11 | 1.3 | 8.5 | Very much | Marked | Success |

[a]Difference in ratings of lofexidine's effectiveness in alleviating various pharmacological effects between day 2 and last day of treatment (0 - no suppression; 10 - complete suppression).
[b]Patient's feeling on "how the drug helped" at final examination.
[c]Physician's evaluation of therapeutic effect of the drug at final examination.
[d]Clinical success is determined by a negative naloxone test.

I claim:

1. A method of alleviating the adverse symptoms associated with opium and heroin withdrawal which comprises the administration of an anti-withdrawal amount of lofexidine or a pharmaceutically acceptable salt thereof to a patient in need thereof.

2. A method according to claim 1 wherein the anti-withdrawal amount is from 0.1 to 1.6 milligrams of lofexidine per day.

3. A method according to claim 1 wherein the adverse symptoms are those associated with opium withdrawal.

4. A method according to claim 1 wherein the adverse symptoms are those associated with heroin withdrawal.

5. A method of alleviating the adverse symptoms associated with barbiturate withdrawal which comprises the administration of an anti-withdrawal amount of lofexidine or a pharmaceutically acceptable salt thereof to a patient in need thereof.

6. A method according to claim 5 wherein the anti-withdrawal amount is from 0.1 to 1.6 milligrams of lofexidine per day.

7. A method of alleviating the adverse symptoms associated with benzodiazepine withdrawal which comprises the administration of an anti-withdrawal amount of lofexidine or a pharmaceutically acceptable salt thereof to a patient in need thereof.

8. A method according to claim 7 wherein the anti-withdrawal amount is from 0.1 to 1.6 milligrams of lofexidine per day.

* * * * *